(12) United States Patent
Shimada et al.

(10) Patent No.: US 6,629,966 B2
(45) Date of Patent: *Oct. 7, 2003

(54) DISPOSABLE PULL-ON DIAPER

(75) Inventors: Takaaki Shimada, Kagawa-ken (JP); Seiji Suzuki, Kagawa-ken (JP)

(73) Assignee: Uni-Charm Corp., Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/939,433

(22) Filed: Aug. 24, 2001

(65) Prior Publication Data
US 2002/0026172 A1 Feb. 28, 2002

(30) Foreign Application Priority Data
Aug. 24, 2000 (JP) .......................... 2000-297573

(51) Int. Cl.⁷ .......................... A61F 13/15; A61F 13/20
(52) U.S. Cl. ................. 604/385.13; 604/389; 604/396; 604/391
(58) Field of Search .................. 604/386, 389–396, 604/385.13, 385.201, 385.02

(56) References Cited

U.S. PATENT DOCUMENTS

| | | | | |
|---|---|---|---|---|
| 3,776,232 A | * | 12/1973 | Schaar | 604/390 |
| 3,954,106 A | * | 5/1976 | Tritsch | 604/390 |
| 3,995,639 A | * | 12/1976 | Cheslow | 604/396 |
| 4,090,516 A | * | 5/1978 | Schaar | 604/390 |
| 4,209,016 A | * | 6/1980 | Schaar | 604/390 |
| 4,211,226 A | * | 7/1980 | Schaar | 604/390 |
| 4,909,802 A | * | 3/1990 | Ahr et al. | 604/392 |
| 5,358,500 A | * | 10/1994 | Lavon et al. | 604/390 |
| 5,575,784 A | * | 11/1996 | Amesm Ooten et al. | 604/385.13 |
| 5,603,794 A | * | 2/1997 | Thomas | 604/390 |
| 5,807,371 A | * | 9/1998 | Toyada et al. | 604/389 |
| 6,069,306 A | * | 5/2000 | Isvan et al. | 604/389 |
| 6,264,644 B1 | * | 7/2001 | Igave et al. | 604/390 |
| 6,475,205 B2 | * | 11/2002 | Shimada et al. | 604/385.13 |
| 2002/0004655 A1 | * | 1/2002 | Shimada et al. | 604/385.03 |
| 2002/0049420 A1 | * | 4/2002 | Suzuki | 604/85.13 |

FOREIGN PATENT DOCUMENTS

| | | | | |
|---|---|---|---|---|
| EP | 0623330 | * | 11/1994 | ........... 604/389 |
| JP | 9-253123 | | 9/1997 | |
| JP | 9-253124 | | 9/1997 | |

* cited by examiner

Primary Examiner—Karin Reichle
(74) Attorney, Agent, or Firm—Butzel Long

(57) ABSTRACT

A disposable pull-on diaper that includes a pair of tape fasteners which are adapted to hold the diaper in a rolled-up state. The tape fasteners are provided at transversely opposite side edges of a rear waist region so as to extend along the side edges in a longitudinal direction. Each of the tape fasteners has an upper end portion lying adjacent a waist-opening and a lower end portion lying adjacent an associated leg-opening. The upper end portions of the tape fasteners are bonded to the diaper by bonding zones which extend obliquely inward in a waist-surrounding direction from the transversely opposite side edges of the rear waist region toward the lower end portions.

7 Claims, 5 Drawing Sheets

DISPOSABLE PULL-ON DIAPER

BACKGROUND OF THE INVENTION

This invention relates to a disposable pull-on diaper provided with tape fasteners, which tape fasteners are used to fasten the used diaper in rolled up state for its disposal.

Japanese Patent Application Publications Nos. 1997-253123A and 1997-253124A describe a disposable pull-on diaper comprising a liquid-pervious topsheet, a liquid-impervious backsheet and a liquid-absorbent core disposed between these two sheets so as to configure front and rear waist regions opposed to each other and a crotch region extending between these waist regions. In the rear waist region, tape fastener(s) is(are) attached to the outer surface of the backsheet so that the used diaper may be fastened in a rolled-up state for its disposal.

In the diaper described in Japanese Patent Application Publication No. 1997-253123A, the tape fastener is formed with a single tape strip extending in a waist-surrounding direction and bonded at the middle zone in its longitudinal direction to the diaper. The remaining right and left side portions of the tape strip are folded up so that these portions may be unfolded rightward and leftward in the waist-surrounding direction. The right and left side portions are formed with pressure-sensitive adhesive zones serving to hold these portions in their folded-up state.

In the diaper described in Japanese Patent Application Publication No. 1997-253124A, the tape fasteners are formed with a pair of adhesive tape strips extending in parallel to each other in the waist-surrounding direction and vertically spaced apart from each other.

For disposal of such diaper disclosed in the Publications after use, the diaper is rolled up from the opposite side edges in a transverse direction toward the tape fastener(s) and then the tape fastener(s) is (are) wound round the diaper in the vicinity of its middle zone and anchored on the outer surface of the backsheet by means of pressure-sensitive adhesive. The rolled-up diaper is fastened in this manner and held in the rolled-up state.

The prior art diaper disclosed in the above Publications requires its user to roll up the diaper from both of its side edges toward the tape fastener(s) and then wind the tape fastener(s) around the rolled-up diaper. Consequently, much time and labor are required for the operation of rolling up the diaper and for the operation of winding the tape fastener(s) around this rolled-up diaper. In addition, it is impossible for such prior art diaper to close the waist-opening using the tape fasteners and there is always an anxiety that excretion and/or its odor might leak from the waist-opening.

SUMMARY OF THE INVENTION

It is an object of this invention to provide a disposable pull-on diaper that is adapted to be easily rolled up and fastened in such a rolled-up state for its disposal after use without any likelihood that excretion and/or its odor might leak from the waist-opening and/or the pair of leg-openings.

According to this invention, there is provided a disposable pull-on diaper comprising first and second waist regions opposed to each other and a crotch region extending between these waist regions so that the first and second waist regions are connected together in the vicinity of transversely opposite side edges thereof to define a waist-opening and a pair of leg-openings. A pair of tape fasteners adapted to fasten the diaper in its rolled-up state are attached to an outer surface of the diaper. The tape fasteners are formed on inner surfaces thereof that are opposed to the outer surface of the diaper with anchoring means.

The tape fasteners are provided in the vicinity of the transversely opposite side edges of one of the first and second waist regions so as to extend in a longitudinal direction in parallel to the transversely opposite side edges. The tape fasteners respectively have upper end portions which lie adjacent the waist-opening and lower end portions which lie adjacent the leg-openings. The upper end portions of the tape fasteners are bonded to the diaper by means of bonding zones that are located in the vicinity of a peripheral edge of the waist-opening, and the bonding zones extend obliquely inward in the waist-surrounding direction from the transversely opposite side edges toward the lower end portions of the tape fasteners.

According to one embodiment of this invention, the upper end portions of each of the tape fasteners lie inward in the waist-surrounding direction with respect to the lower end portions of each of the tape fasteners which obliquely extend from their upper end portions toward their lower end portions so as to be progressively more spaced apart from each other.

According to another embodiment of this invention, an elastically stretchable member associated with the waist-opening extending in the waist-surrounding direction is attached under tension to the peripheral edge portion of the waist-opening and the bonding zones overlap at least a part of the elastically stretchable member associated with the waist-opening.

According to still another embodiment of this invention, the anchoring means are formed of pressure-sensitive adhesive agents or hooked members that are applied on the tape fasteners, or and release sheets that are adapted for temporarily retaining the tape fasteners are attached to the outer surface of the diaper in the vicinity of the transversely opposite side edges.

DETAILED DESCRIPTION OF THE PREFERRED EMBODIMENTS

Details of a disposable pull-on diaper according to this invention will be more fully understood from the description given hereunder with reference to the accompanying drawings.

Figure 1:
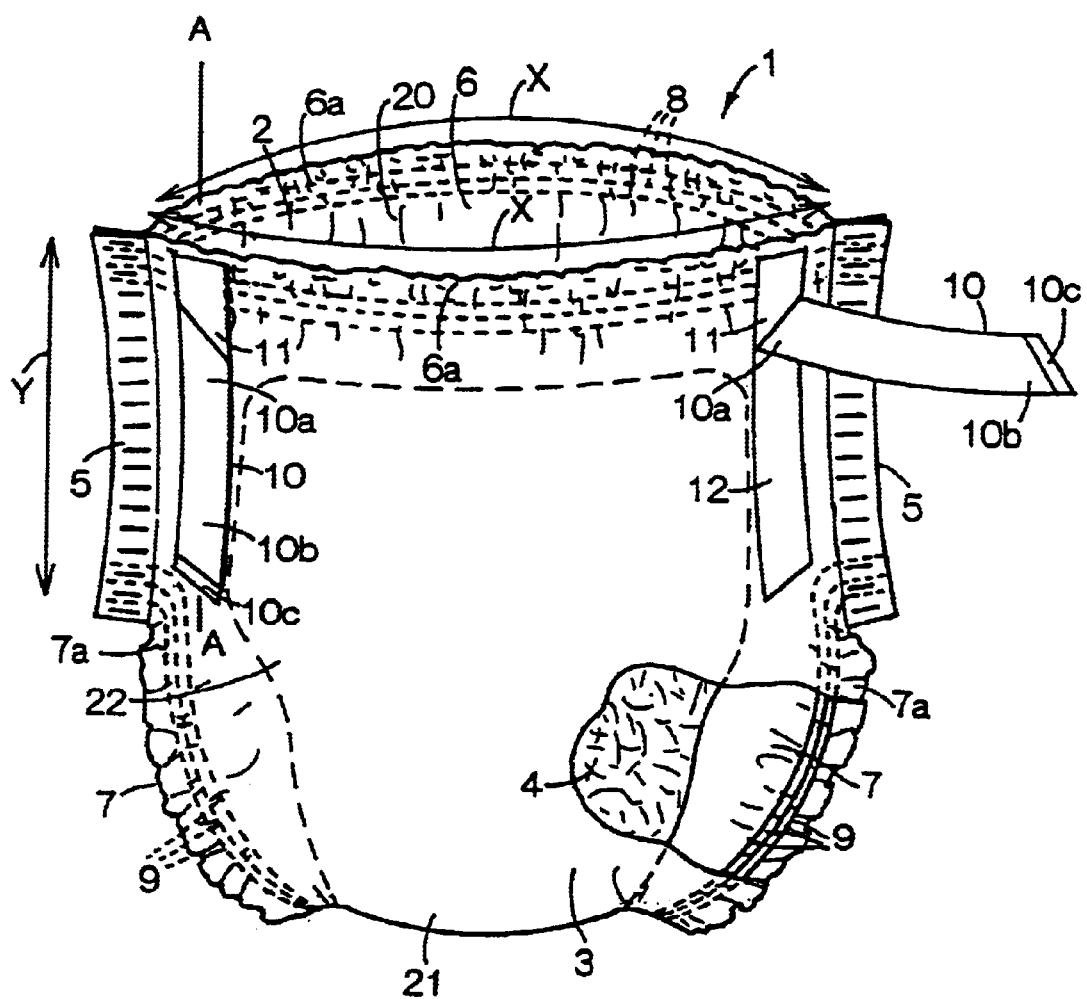
FIG. 1 is a perspective view showing a disposable pull-on diaper as viewed from the side of the rear waist region and as partially broken away.
Figure 2:
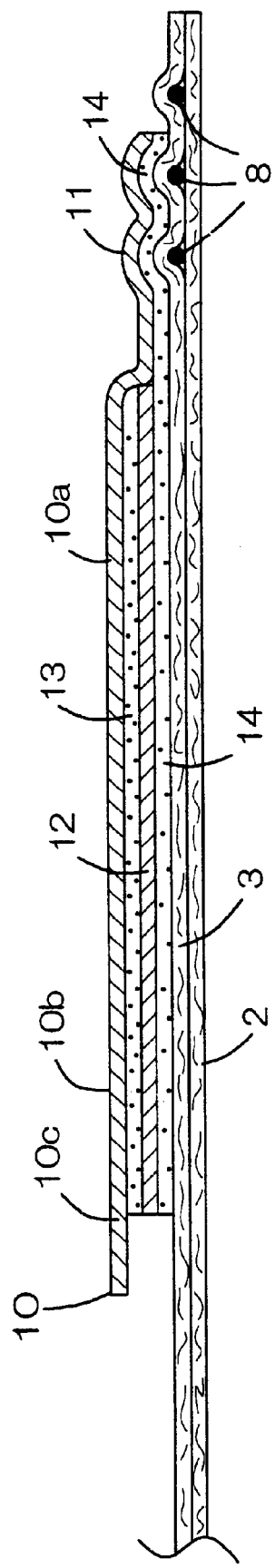
FIG. 2 is a sectional view taken along a line I—I in FIG. 1.

FIG. 1 is a perspective view showing a disposable pull-on diaper 1 as viewed from the side of a rear waist region 22 and as partially broken away and FIG. 2 is a sectional view taken along section line I—I in FIG. 1. In FIG. 1, one of tape fasteners 10 is shown as being separated from a release sheet 12. Surfaces of top sheet and backsheet 2, 3, the tape fasteners 10, the release sheets 12 and the other elements which face core 4 will be referred to herein as "inner surfaces" and surfaces of the components 2, 3, 10, 12 which do not face the core 4 will be referred to herein as "outer surfaces". A waist-surrounding direction is indicated by an arrow X and a longitudinal direction is indicated by an arrow Y.

The diaper 1 basically comprises the liquid-pervious topsheet 2, the liquid-impervious backsheet 3 and the liquid-absorbent core 4 disposed between these sheets 2, 3 and entirely covered with and bonded to water-pervious tissue paper (not shown). The core 4 is bonded to the inner surface of the topsheet 2 and/or the backsheet 3 with the tissue paper therebetween.

The diaper 1 is composed of front and rear waist regions 20, 22 opposed to each other and a crotch region 21 extending between these waist regions 20, 22. The front and rear waist regions 20, 22 are put flat and bonded together in the vicinity of transversely opposite side edges 5 of the respective waist regions 20, 22 which edge extend in a longitudinal direction so as to define a waist-opening 6 and a pair of leg-openings 7.

Along a peripheral edge portion 6a of the waist-opening 6, an elastically stretchable member 8 comprising a plurality of elastic elements extends in the waist-surrounding direction between the top sheet and backsheet 2, 3 and is bonded under tension to the inner surface of the topsheet 2 and/or the backsheet 3. Along a peripheral edge portion 7a of each leg-opening 7, an elastically stretchable member 9 comprising a plurality of elastic elements extends in a thigh-surrounding direction between the topsheet and backsheet 2, 3 and is bonded under tension to the inner surface of the topsheet 2 and/or the backsheet 3. Consequently, the diaper 1 is elastically stretchable in the circumferential directions of the waist-opening and leg-openings 6, 7 along the peripheral edge portions 6a, 7a thereof. Referring to FIG. 1, a plurality of gathers are formed along the peripheral edge portions 6a, 7a of the waist-opening and leg-openings 6, 7 as the elastic members 8, 9 contract.

In the vicinity of the transversely opposite side edges 5 in the rear waist region 22, a pair of tape fasteners 10 are attached to the outer surface of the backsheet 3 so that the used diaper 1 may be fastened by these tape fasteners 10 in a rolled-up state. The tape fasteners 10 are made of a flexible, but non-stretchable, plastic sheet and extend in parallel to the transversely opposite side edges 5 in the longitudinal direction.

Each of the tape fasteners 10 has an upper end portion 10a lying in the vicinity of the peripheral edge portion 6a of the waist-opening 6 and a lower end portion 10b lying in the vicinity of the peripheral edge portion 7a of the leg-opening 7. Each of the tape fasteners 10 has its upper end portion 10a bonded to the outer surface of the backsheet 3 by means of a bonding zone 11 extending in the waist-surrounding and longitudinal directions. Each tape fastener 10 is coated on its inner surface with a pressure-sensitive adhesive agent 13. The lower end portion 10b of each tape fastener 10 is formed with a grip 10c that is not coated with the pressure-sensitive adhesive agent 13.

The bonding zones 11 overlap the elastic member 8 associated with the waist-opening 6 and lower edges of the respective bonding zones 11 obliquely extend inward from the transversely opposite side edges 5 of the rear waist region 22 toward the lower end portions 10b in the waist-surrounding direction. In the bonding zones 11, the upper end portions 10a are bonded to the backsheet 3 by means of adhesive agent 14. While the bonding zones 11 are illustrated as they completely covering the elastic member 8 associated with the waist-opening 6, the desired effect may be achieved by placing the bonding zones 11 so as to cover at least one elastic element of the elastic member 8.

Release sheets 12 for temporarily bonding of the tape fasteners 10 are disposed between the tape fasteners 10 and the backsheet 3. The release sheets 12 are made of a flexible plastic sheet and have inner surfaces that are bonded to the outer surface of the backsheet 3 by means of adhesive agent 14. The tape fasteners 10 are temporarily bonded to the outer surface of the release sheets 12 by means of pressure-sensitive adhesive agent 13. Hot melt adhesive is preferably used as the adhesive agent 14. The tape fasteners 10 as well as the release sheets 12 may be bonded to the backsheet 3 using a technique of welding, instead of using an adhesive agent.

Figure 3:
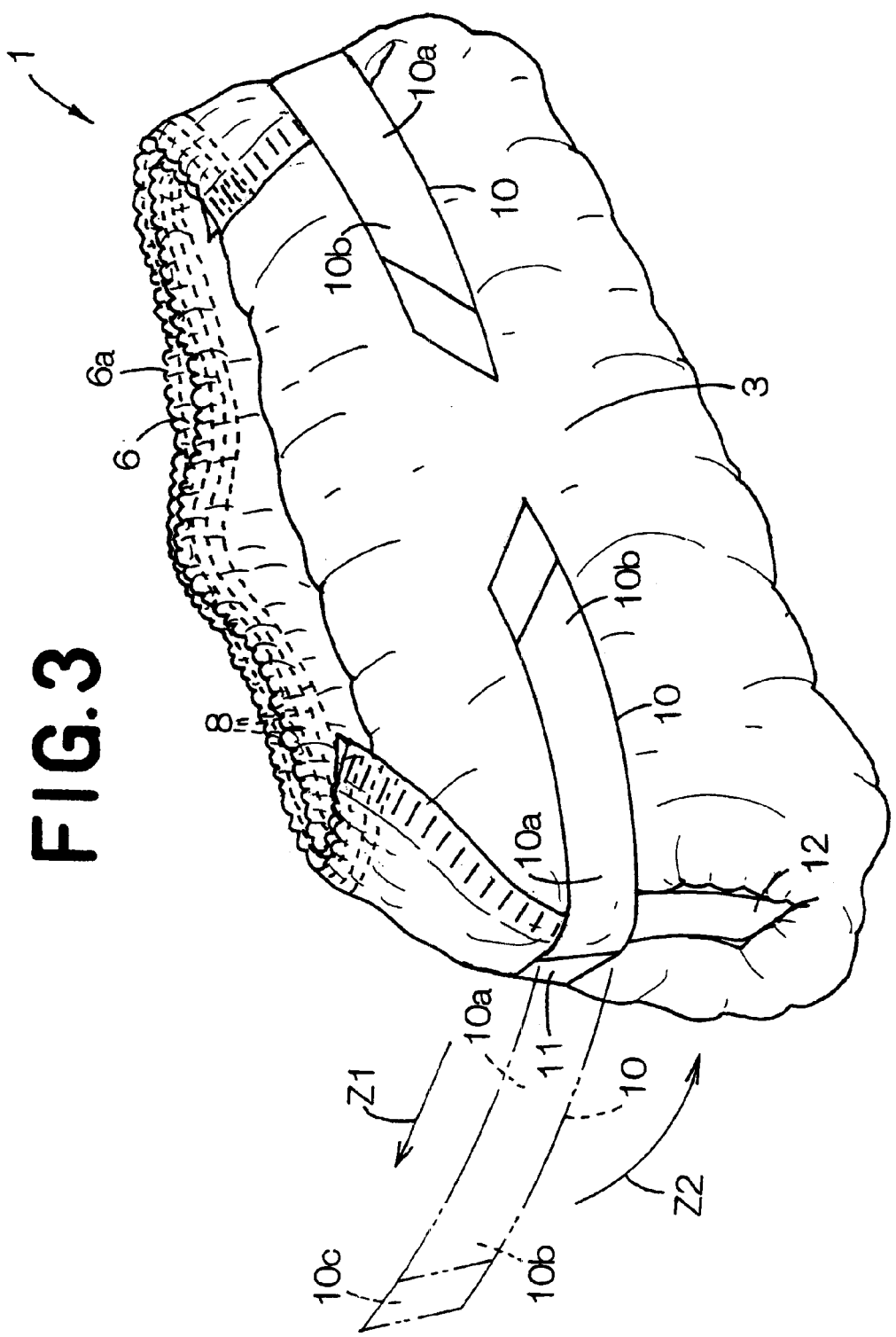
FIG. 3 is a perspective view showing the diaper of FIG. 1 as rolled up for its disposal.

FIG. 3 is a perspective view showing the diaper 1 of FIG. 1 as rolled up for its disposal, in which one of the tape fasteners 10 has been peeled off from the release sheet 12 as indicated by chain lines. The diaper 1 has been rolled up in the longitudinal direction from the crotch region 21 toward the waist-opening 6 with the front waist region 20 inside. Having been rolled up, the waist-opening 6 lies on the exterior of the diaper 1 and the tape fasteners 10 are anchored on the outer surface of the backsheet 3 by means of pressure-sensitive adhesive agent 13.

To fasten the rolled-up diaper 1 with the tape fasteners 10, the tape fasteners 10 are peeled off from the respective release sheets 12 with the grips 10c of the respective fasteners 10 held by one's fingers. Then, the tape fasteners 10 are pulled outwardly of the diaper 1 as indicated by an arrow Z1, simultaneously wound around the rolled-up diaper in a direction indicated by an arrow Z2 and pressed against the outer surface of the backsheet 3.

The lower edges of the respective bonding zones 11 extend obliquely of the diaper 1 and therefore the lower end portions 10b of the respective tape fasteners 10 extend outwardly of the diaper 1 as the tape fasteners 10 are peeled off from the respective release sheets 12. In the case of the diaper 1 according to this embodiment, after the tape fasteners 10 have been peeled off from the respective release sheets 12, the tape fasteners 10 can be easily anchored on the rolled up diaper 1 merely by guiding the tape fasteners 10 in the direction indicated by the arrow Z2 without need to change the directions of the respective tape fasteners 10 and then pressing the tape fasteners 10 against the outer surface of the backsheet 3.

In the case of this diaper 1, the bonding zones 11 overlap the elastic member 8 associated with the waist-opening 6 so that the elastic member 8 associated with the waist-opening 6 is stretched outwardly of the diaper 1 as the tape fasteners 10 are stretched outwardly of the diaper 1. The tape fasteners 10 may be anchored on the backsheet 3 with the elastic member 8 associated with the waist-opening 6 held under tension to ensure that the waist-opening 6 is reliably closed by a contractile force of the stretched elastic member 8 associated with the waist-opening 6. The peripheral edge 6a of the waist-opening 6 closed in this manner is held in close contact with the outer surface of the backsheet 3.

This embodiment ensures that the diaper 1 can be fastened by the respective tape fasteners 10 in its rolled-up state and that a contractile force of the elastic member 8 associated with the waist-opening 6 will hold the waist-opening 6 in a closed state. Consequently, it is less likely that the waist-opening 6 closed in this manner might be unintentionally reopened and excretion and/or its odor might leak from the waist-opening 6. The peripheral edges 7a of the leg-openings 7 are rolled up together with the diaper 1 and therefore there is no anxiety that the leg-openings 7 might be unintentionally reopened and excretion and/or its odor might leak from these leg-openings 7.

Figure 4:
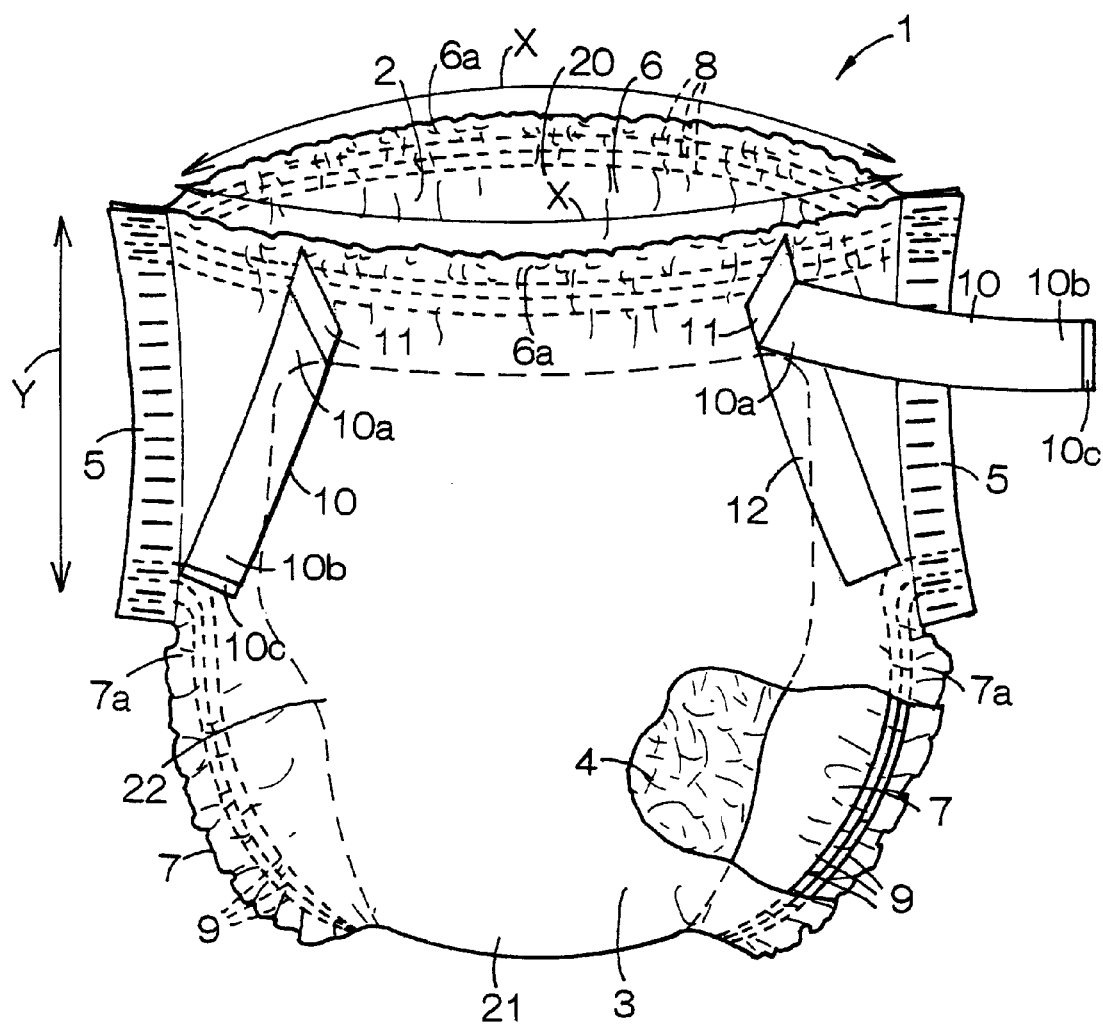
FIG. 4 is a perspective view showing another embodiment of the diaper as viewed from the side of the rear waist region and as partially broken away.
Figure 5:
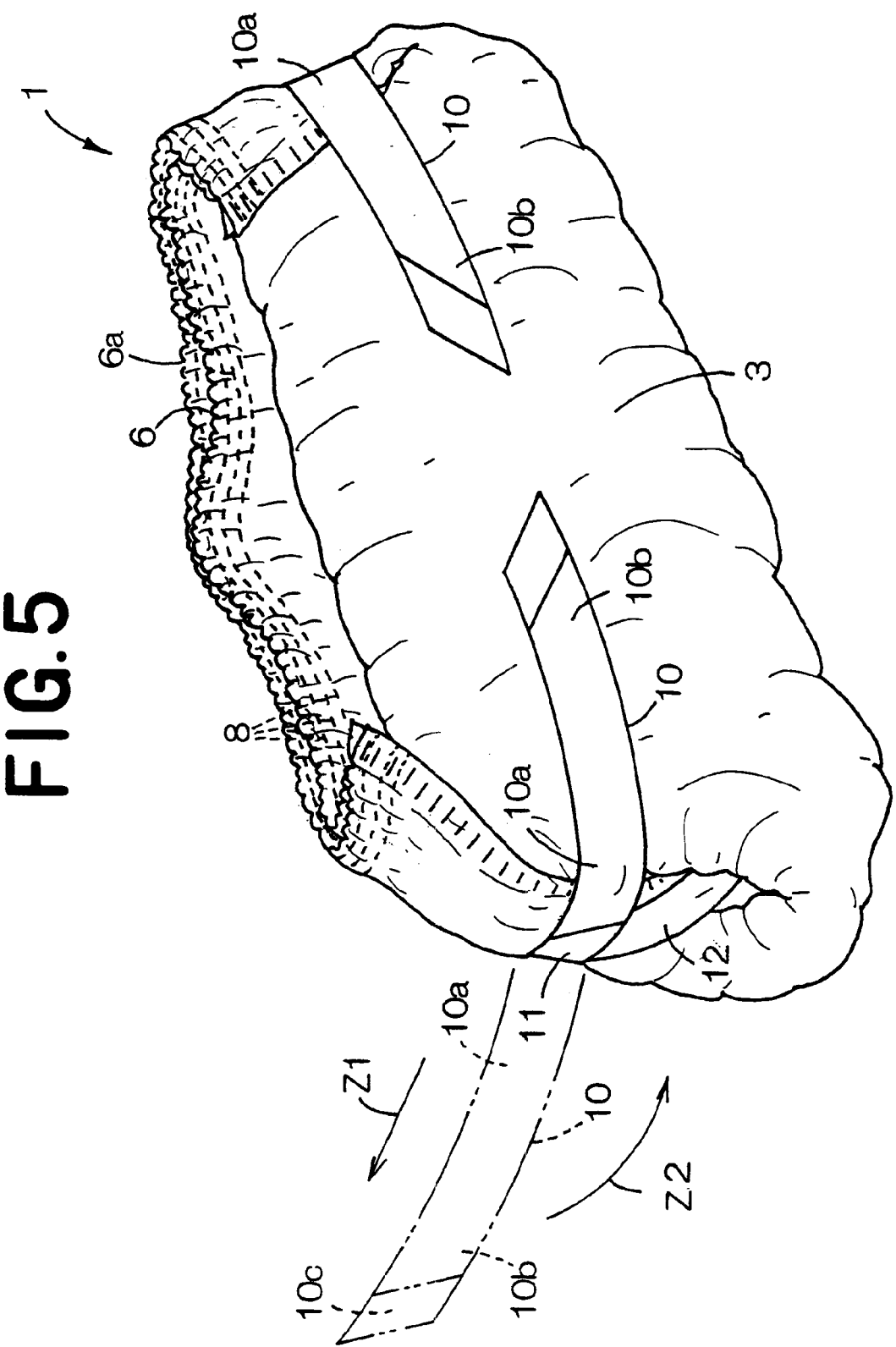
FIG. 5 is a perspective view showing the diaper of FIG. 4 as having been rolled up for its disposal.

FIG. 4 is a perspective view showing another embodiment of the diaper 1 as viewed from the side of the rear waist region 22 and as partially broken away, and FIG. 5 is a perspective view showing the diaper of FIG. 4 as rolled up for its disposal. FIG. 4 shows one of the tape fasteners 10 peeled off from the release sheet 12 and FIG. 5 shows this tape fastener 10 peeled off from the release sheet 12 by chain lines.

The configuration of this diaper 1 is basically similar to that of FIG. 1 and a detailed description thereof will accordingly be eliminated. The diaper 1 of FIG. 4 is distinguished from the diaper 1 of FIG. 1 in that the upper end portion 10a of each tape fastener 10 lies inward with respect to the lower end portion 10b in the waist-surrounding direction and the pair of tape fasteners 10 obliquely extend from the upper end portions 10a toward the lower end portions 10b so that these two tape fasteners 10 are progressively more spaced apart from each other.

The diaper 1 can be rolled up in the longitudinal direction from the crotch region 21 toward the waist-opening 6 with the front waist region 20 inside, as will be apparent from FIG. 5. Having been rolled up, the waist-opening 6 lies on the exterior of the diaper 1 and the tape fasteners 10 are anchored on the outer surface of the backsheet 3 by means of pressure-sensitive adhesive (not shown).

In the diaper 1 according to this alternative embodiment, the pair of tape fasteners 10 obliquely extend from their upper end portions 10a toward their lower end portions 10b so that these tape fasteners 10 are progressively more spaced apart from each other and the lower edges of the respective bonding zones 11 extend from the transversely opposite side edges 5 of the diaper 1 toward the lower edges 10b obliquely inward in the waist-surrounding direction. With such an arrangement, the lower end portions 10b of the respective tape fasteners 10 extend outwardly of the diaper 1 as indicated by the arrow Z1 as the tape fasteners 10 are peeled off from the respective release sheets 12. After the tape fasteners 10 have been peeled off from the respective release sheets 12, the tape fasteners 10 may be placed around the rolled-up diaper in the direction indicated by the arrow Z2 without need to change their directions and then pressed against the outer surface of the backsheet 3.

The diaper 1 of FIG. 4 is similar to the diaper 1 of FIG. 1 in that the elastic member 8 associated with the waist-opening 6 is stretched outwardly of the diaper 1 as the tape fasteners 10 are pulled outward of the diaper 1. In this way, the diaper 1 is held by the respective tape fasteners 10 in the rolled-up state and the waist-opening 6 is held in a closed state under a contractile force of the elastic member 8 associated with the waist-opening 6.

The tape fasteners 10 may be formed from a non-stretchable plastic sheet, elastically stretchable elastomer such as synthetic or natural rubber or such elastomer bonded under tension to a nonwoven fabric.

When backsheet 3 is made of a nonwoven fabric, it is possible to attach a hook member, serving as a component of the so-called mechanical fastener, to the inner surface of the tape fastener 10, instead of coating the inner surface of the tape fastener 10 with a pressure-sensitive adhesive agent. In this case, the hook member is engaged with component fibers of the nonwoven fabric so that the tape fastener 10 may be reliably anchored on the outer surface of the backsheet 3 of the rolled-up diaper 1. When a hook member is attached to the tape fastener 10, it is possible to replace the release sheet 12 with a loop member which may be attached to the outer surface of the backsheet 3 in the vicinity of the side edge 5 of the rear waist region 22. It is also possible to attach the tape fasteners 10 as well as the release sheets 12 to the outer surface of the backsheet 3 in the vicinity of the transversely opposite side edges 5 of the front waist region 20. The topshee t 2 may be formed from a liquid-pervious sheet such as a nonwoven fabric or porous plastic film, preferably from a liquid-pervious hydrophilic sheet. The backsheet 3 may be formed from a hydrophobic nonwoven fabric, a liquid-impervious plastic film or a laminated sheet of a hydrophobic nonwoven fabric and a plastic film, preferably from a breathable but liquid-impervious sheet. It is also possible to use a composite nonwoven fabric consisting of a melt blown nonwoven fabric having a high water-resistance of whose opposite sheet surfaces are sandwiched by two layers of spun bond nonwoven fabric having high strength and flexibility.

The nonwoven fabric may be selected from a group including spun lace-, needle punch-, melt blown-, thermal bond-, spun bond-, chemical bond- and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 4 is a mixture of fluff pulp, high absorption polymer particles and thermoplastic synthetic resin fiber compressed to a desired thickness. The high absorption polymer may be selected from a group including starch-, cellulose-based polymer and synthetic polymer.

Bonding of the topsheet and backsheet 2, 3, the core 4 as well as attaching of the elastic members 8, 9 may be carried out using suitable adhesive such as a hot melt adhesive agent or a technique of welding such as a sonic-sealing or a heat-sealing.

For disposal of the disposable pull-on diaper according to this invention after used, the diaper may be rolled up in the longitudinal direction from the crotch region toward the waist-opening, the tape fasteners may be peeled off from the respective release sheets, then guided around the rolled-up diaper without needing to change their directions and anchored on the outer surface of the rolled up diaper. In this manner the operation of rolling up the used diaper as well as operation of anchoring the tape fasteners on the rolled up diaper can be carried out more easily than in the conventional diaper.

The diaper is reliably held by the tape fasteners in the rolled-up state. The tape fasteners may be anchored to the rolled-up diaper with the elastic member associated with the waist-opening being stretched outwardly of the diaper to ensure that a contractile force of the stretched elastic member associated with the waist-opening functions to hold the waist-opening in closed state. There is no anxiety that the waist-opening might be unintentionally reopened and excretion and/or its odor might leak from the waist-opening.

The peripheral edges of the respective leg-openings are rolled up together with the diaper, so there is no anxiety that these leg-openings might be unintentionally reopened and excretion and/or its odor might leak from these leg-openings.

What is claimed is:

1. A disposable pull-on diaper comprising:

first and second waist regions opposed to each other and a crotch region extending between said first and second waist regions, said first and second waist regions being permanently connected together at respective transversely opposite side edges thereof to define a waist-opening and a pair of leg-openings, a pair of tape fasteners adapted to fasten said diaper after use in a rolled-up state, said pair of tape fasteners being attached to an outer surface of said diaper, each of said tape fasteners being formed on an inner surface with means for anchoring said diaper in the rolled-up state, said tape fasteners provided adjacent said transversely opposite side edges, respectively, in one of said first and second waist regions so as to extend in a longitudinal direction thereof in parallel to said transversely opposite side edges, said tape fasteners respectively having upper end portions which lie adjacent said waist-opening and releasable lower end portions which lie adjacent said leg-openings, said lower end portions including said anchoring means, said upper end portions of said pair of tape fasteners being permanently bonded to said diaper by means of respective bonding zones in a vicinity of a peripheral edge portion of said waist-opening, and said bonding zones respectively having lower edges extending obliquely inward in a circumferential direction of the waist opening from said transversely opposite side edges in the vicinity of said waist opening toward said lower end portions of said pair of tape fasteners.

2. The diaper according to claim 1, further comprising an elastically stretchable member associated with said waist-opening that extends in said circumferential direction of the waist opening and is attached under tension to the peripheral edge portion of said waist-opening and said bonding zones overlapping at least a part of said elastically stretchable member.

3. The diaper according to claim 1, wherein said anchoring means comprise pressure-sensitive adhesive agents on said tape.

4. The diaper according to claim 3, further comprising release sheets adapted for temporarily retaining said tape fasteners, said release sheets being attached to the outer surface of said diaper adjacent said transversely opposite side edges.

5. The diaper according to claim 1, wherein said anchoring means comprise hook members.

6. The diaper according to claim 5, further comprising release sheets adapted for temporarily retaining said tape fasteners, said release sheets being attached to the outer surface of said diaper adjacent of said transversely opposite side edges.

7. A disposable pull-on diaper comprising:

first and second waist regions opposed to each other and a crotch region extending between said first and second waist regions, said first and second waist regions being permanently connected together at respective transversely opposite side edges thereof to define a waist-opening and a pair of leg-openings, a pair of tape fasteners adapted to fasten said diaper after use in a rolled-up state, said pair of tape fasteners being attached to an outer surface of said diaper, each of said tape fasteners being formed on an inner surface with means for anchoring said diaper in the rolled-up state, said tape fasteners provided adjacent said transversely opposite side edges, respectively, in one of said first and second waist regions so as to extend in a longitudinal direction thereof along said transversely opposite side edges, said tape fasteners respectively having upper end portions which lie adjacent said waist-opening and releasable lower end portions which lie adjacent said leg-openings, said lower end portions including said anchoring means, said upper end portions of said pair of tape fasteners being permanently bonded to said diaper by means of respective bonding zones in a vicinity of a peripheral edge portion of said waist-opening, said bonding zones respectively having lower edges extending obliquely inward in a circumferential direction of the waist opening from said transversely opposite side edges in the vicinity of said waist opening toward said lower end portions of said pair of tape fasteners, and wherein said upper end portions lie inward in said circumferential direction with respect to said lower end portions of said tape fasteners, respectively, and said tape fasteners extend obliquely from their upper end portions toward their lower end portions so as to be progressively more spaced apart from each other.

* * * * *